(12) United States Patent
Gückel et al.

(10) Patent No.: US 7,803,972 B2
(45) Date of Patent: Sep. 28, 2010

(54) SHELL CATALYST, IN PARTICULAR FOR OXIDATION OF METHANOL TO FORMALDEHYDE, AND ALSO METHOD FOR PRODUCTION THEREOF

(75) Inventors: Christian Gückel, Paramus, NJ (US); Klaus Wanninger, Kolbermoor (DE); Marvin Estenfelder, Karlsruhe (DE); Claudia Fischer, Feldkirchen (DE); Uwe Dürr, Fürth (DE)

(73) Assignee: Süd-Chemie AG, Munich (DE)

( * ) Notice: Subject to any disclaimer, the term of this patent is extended or adjusted under 35 U.S.C. 154(b) by 51 days.

(21) Appl. No.: 12/094,288

(22) PCT Filed: Nov. 23, 2006

(86) PCT No.: PCT/EP2006/011256

§ 371 (c)(1),
(2), (4) Date: Sep. 23, 2008

(87) PCT Pub. No.: WO2007/059974

PCT Pub. Date: May 31, 2007

(65) Prior Publication Data

US 2010/0016640 A1 Jan. 21, 2010

(30) Foreign Application Priority Data

Nov. 23, 2005 (DE) .................. 10 2005 055 827
Nov. 23, 2005 (EP) .................. 05025497

(51) Int. Cl.
*C07C 45/37* (2006.01)
*B01J 21/00* (2006.01)

(52) U.S. Cl. .................. 568/471; 568/472; 502/241; 502/248

(58) Field of Classification Search .................. 502/241, 502/248; 568/471, 472
See application file for complete search history.

(56) References Cited

U.S. PATENT DOCUMENTS

| 3,852,361 | A | 12/1974 | Haas |
| 3,975,302 | A | 8/1976 | Courty |
| 3,978,136 | A | 8/1976 | Friedrich |
| 4,181,629 | A | 1/1980 | Cairati |
| 4,521,618 | A | 6/1985 | Arntz |
| 4,539,409 | A | 9/1985 | Arntz |
| 4,621,072 | A | 11/1986 | Arntz |
| 4,656,157 | A | 4/1987 | Hofmann |
| 5,217,936 | A | 6/1993 | Sarup |
| 6,274,763 | B1 | 8/2001 | Ruedinger |
| 6,518,220 | B2 | 2/2003 | Walsdorff |
| 6,528,683 | B1 | 3/2003 | Heidemann |
| 6,624,114 | B1 | 9/2003 | Eberle |
| 6,700,000 | B1 | 3/2004 | Heidemann |
| 7,338,918 | B2 | 3/2008 | Neto |
| 2006/0235232 | A1 | 10/2006 | Neto |
| 2007/0041795 | A1 | 2/2007 | Neto |
| 2007/0135302 | A1 | 6/2007 | Neto |
| 2007/0142677 | A1 | 6/2007 | Olbert |
| 2008/0008877 | A1 | 1/2008 | Harth |

FOREIGN PATENT DOCUMENTS

| DE | 4006935 | 9/1991 |
| DE | 19709589 | 9/1998 |
| EP | 0001570 | 5/1979 |
| EP | 0294775 | 12/1988 |
| EP | 1674156 | 6/2006 |
| WO | WO2004035473 | 4/2004 |

OTHER PUBLICATIONS

English translation of International Preliminary Report on Patentability pertaining to international application No. PCT/EP2006/011256, filed in the U.S. Appl. No. 12/094,288. This application may contain information material to the patentability of the current application.

*Primary Examiner*—Sikarl A Witherspoon
(74) *Attorney, Agent, or Firm*—Scott R. Cox

(57) ABSTRACT

The invention relates to a coated catalyst, especially for oxidation of methanol to formaldehyde, which, on an inert, preferably essentially nonporous, support body, has at least one coating which comprises, before the removal of the organic fractions of components b) and c): (a) oxides, or precursor compounds convertible to the corresponding oxides, of molybdenum and iron, where the molar ratio of Mo:Fe is between 1:1 and 5:1, and optionally further metallic components or metal oxide components or precursor compounds convertible to the corresponding oxides, (b) at least one organic binder, preferably an aqueous dispersion of copolymers, especially selected from vinyl acetate/vinyl laurate, vinyl acetate/ethylene, vinyl acetate/acrylate, vinyl acetate/maleate, styrene/acrylate or mixtures thereof, and (c) at least one further component selected from the group consisting of $SiO_2$ sol or precursors thereof, $Al_2O_3$ sol or precursors thereof, $ZrO_2$ sol or precursors thereof, $TiO_2$ sol or precursors thereof, waterglass, MgO, cement, monomeric, oligomeric or polymeric silanes, alkoxysilanes, aryloxysilanes, acryloyloxysilanes, aminosilanes, siloxanes or silanols. Additionally described is a process for preparing the catalyst and its preferred use.

35 Claims, 1 Drawing Sheet

Figure 1:
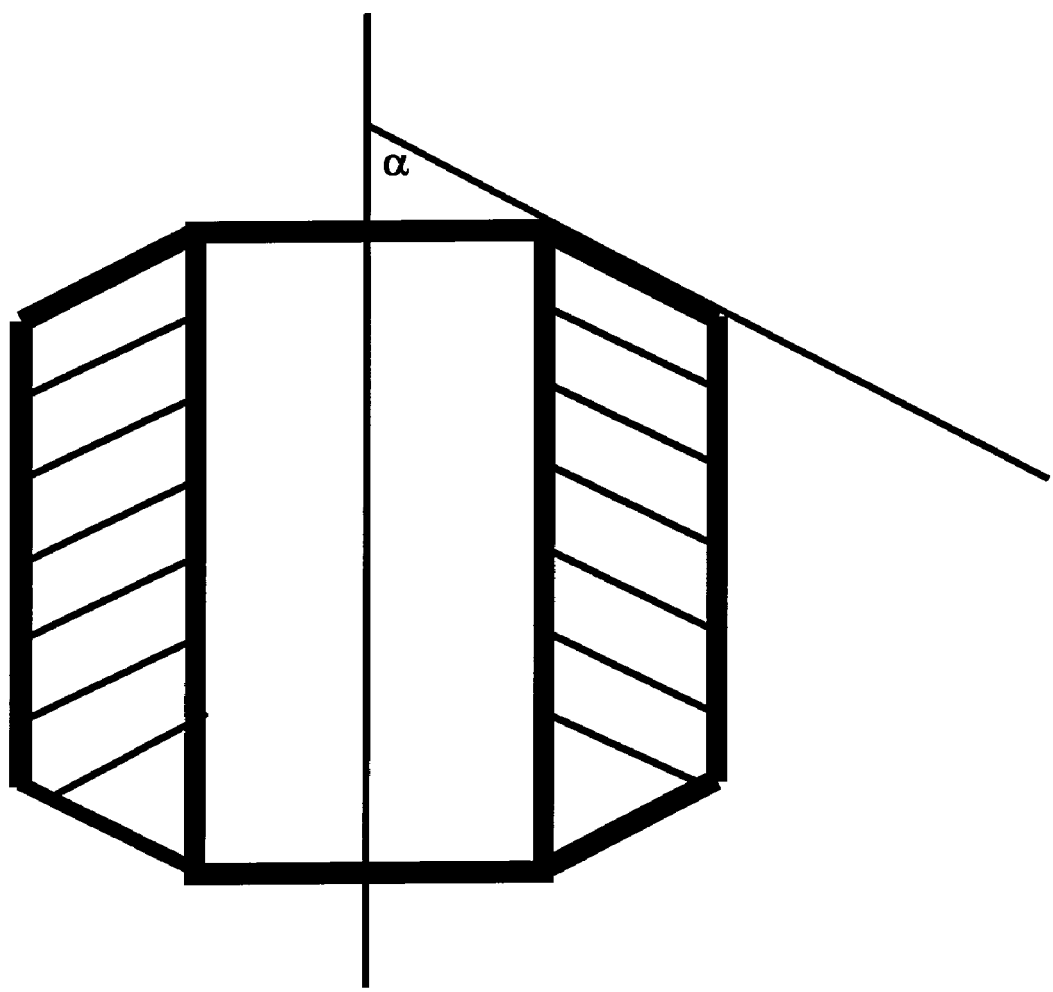

SHELL CATALYST, IN PARTICULAR FOR OXIDATION OF METHANOL TO FORMALDEHYDE, AND ALSO METHOD FOR PRODUCTION THEREOF

The present invention relates to a shell catalyst, specifically to a coated catalyst, especially for oxidizing methanol to formaldehyde, which, on an inert, preferably essentially nonporous, support body, has a coating composed of a composition which, as well as an active material, comprises an adhesion promoter composition which comprises at least one organic binder and at least one further, at least partly inorganic, adhesion-promoting component, especially a sol component.

Molybdenum-iron catalysts for partial oxidation of methanol to formaldehyde have already been known for some time.

The atomic ratios between molybdenum and iron can vary in these known catalysts. Moreover, a portion of the active components can be replaced partly by titanium, antimony, tin, nickel, chromium, cerium, aluminum, calcium, magnesium, vanadium, niobium, silver and/or manganese. Such catalysts comprising, for example, titanium are known for the partial oxidation of methanol to formaldehyde, for example, from U.S. Pat. No. 3,978,136. However, in contrast to the inventive catalyst, this is not a coated catalyst.

Coated catalysts are understood to mean catalysts which arise through coating of a (nonporous) support body with a porous layer of the actual active material.

In contrast, in impregnation processes, the catalytically active sites (frequently noble metals such as Pd, Pt, Au, Ag etc.) are applied as a solution in disperse form to a porous support (frequently: $SiO_2$, $Al_2O_3$, $TiO_2$, $ZrO_2$, carbon, $Nb_2O_5$ etc.). In the catalysts prepared by the impregnation process, chemical-physical interactions usually exist between support and active sites, which have a crucial influence on the catalytic events. In contrast, in the case of coated catalysts, the support body serves merely for structural support. In contrast to impregnated catalysts, in which the active elements are present in dispersed form in the porous support—if appropriate also in an outer shell present in the support (=shell catalyst)—the (nonporous or essentially nonporous) support body in the coated catalyst is enveloped by the active material.

U.S. Pat. No. 3,975,302 describes an Fe/Mo catalyst prepared by the impregnation process for the oxidation of methanol to formaldehyde. According to this, iron and molybdenum are dissolved in water as $MoO_4^{2-}$ and $Fe^{3+}$ salts and then impregnated onto a porous support with a BET surface area of from 1 to 20 $m^2/g$.

U.S. Pat. No. 4,181,629 also describes a catalyst for the oxidation of methanol to formaldehyde, which is prepared by impregnation in a fluidized bed process.

EP-A-0 068 192 relates to an abrasion-resistant shell catalyst, for which the preferred binders in the shell composition are specified as glucose or urea in aqueous solution.

EP-A-0 294 775 relates to a process for preparing a shell catalyst by spray application of the catalytically active material onto moving support particles at temperatures of from 100 to 600° C.

WO 98/23371 describes a coated catalyst for preparing acetic acid by gas phase oxidation of unsaturated $C_4$ carbons. The catalyst comprises an inert nonporous support body to whose surface a catalytically active mixed oxide material has been applied. This material comprises (a) one or more oxides from the group of titanium oxide, zirconium dioxide, tin dioxide, aluminum oxide, and (b) based on the weight of component (a) and per $m^2/g$ of specific surface area of component (a), from 0.1 to 1.5% by weight of vanadium pentoxide. A portion of vanadium pentoxide, preferably from 10 to 90% by weight, can be replaced by one or more oxides of molybdenum, chromium and antimony. If appropriate, as an additional component (b), one or more oxides of alkali metals, elements of main group 5 and 6 of the Periodic Table of the elements and the transition metals may also be present. Among other elements, iron is also mentioned. The proportion of these dopants is from 0.05 to 15% by weight, calculated as oxide and based on the total weight of component (b). The catalytically active mixed oxide material may optionally also contain 10 to 50% by weight, based on the total weight of the catalytically active mixed oxide material, of inert diluents such as silicon dioxide or silicon carbide. The binders used are organic binders. To prepare the catalysts, the active components are ground with addition of water. Subsequently, a copolymer dispersion of vinyl acetate and vinyl laurate is added. The finished suspension is applied to steatite spheres with evaporation of the water. The examples do not describe any catalyst which simultaneously comprises molybdenum and iron.

WO 99/62637 describes a process for preparing shell catalysts for the catalytic gas phase oxidation of aromatic hydrocarbons. The catalyst consists of a support core and catalytically active metal oxides applied thereto in shell form. The catalyst is prepared by spraying an aqueous active composition suspension onto the hot support material. The active composition suspension comprises an organic binder. This binder is formed from (A) a polymer which is prepared from (a) from 5 to 100% by weight of monomers in the form of ethylenically unsaturated acid anhydrides or ethylenically unsaturated dicarboxylic acids whose carboxyl groups can form an anhydride, and (b) from 0 to 95% by weight of monoethylenically unsaturated monomers, with the proviso that the monomers (a) and (b) have an average of at most 6 carbon atoms which are not functionalized with oxygen-containing groups, and (B) an alkanolamine having at least 2 OH groups, at most 2 nitrogen atoms and at most 8 carbon atoms, where the weight ratio of (A):(B) is from 1:0.05 to 1:1. The catalytically active constituent used in the catalytically active composition is generally, as well as titanium dioxide in its anatase modification, vanadium pentoxide. In addition to these main constituents, a multitude of other oxidic compounds may be present, which, as promoters, influence the activity and selectivity of the catalyst. Examples of promoters include the alkali metal oxides, thallium(I) oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide and phosphorus pentoxide. Suspension of the active composition is applied to the support by spraying. This can be done, for example, in a coating drum or in a fluidized bed coater. The examples do not describe any catalyst which simultaneously possesses molybdenum and iron. Apart from the organic binder, no further binder is used.

U.S. Pat. No. 5,217,936 describes a catalyst for the preparation of aldehydes from the corresponding alcohols, especially of formaldehyde from methanol, wherein the catalytically active composition is applied to a monolithic support. The active composition may, as well as molybdenum oxide, also comprise oxides of chromium, vanadium, aluminum, iron, tungsten, manganese and mixtures thereof. In order to improve the binding of the active composition to the monolithic support, the active composition may comprise a binder. Suitable binders specified are silicon dioxide and titanium dioxide. The use of organic binders is not described.

EP 1 108 470 A1 describes supported catalysts which are suitable for the gas phase oxidation of hydrocarbons. The supported catalysts consist of an active composition which is applied on an inert support body. The support body has the shape of a ring in which one or more notches are introduced on the upper and/or lower flat side of the ring.

WO 99/61433 describes a process for preparing phthalic anhydride by catalytic gas phase oxidation of xylene or naphthalene, where a reactor which comprises at least three layers of a shell catalyst one on top of another, which have increasing activity from the gas inlet side toward the gas outlet side of the reactor, is used. The active composition is formed from oxides of vanadium and of antimony, of phosphorus, of the alkali metals and of titanium. The activity is adjusted by the amount of the active composition applied to the support bodies and by the content of alkaline metal in the active composition. The catalyst is prepared by spraying an aqueous suspension of the active composition onto inert support bodies, for example in a coating drum or in a fluidized bed coater. In order to reduce losses of active composition in the course of coating, the suspension may comprise an organic polymer as a binder. The use of inorganic binders is not described.

DE 10 2004 014 918 describes a catalyst comprising a silver-vanadium oxide phase and a promoter phase based on titanium dioxide and vanadium pentoxide, which is suitable for the preparation of aldehydes, carboxylic acids and carboxylic anhydrides from aromatic or heteroaromatic hydrocarbons by gas phase oxidation. The catalyst is preferably configured as a shell catalyst, the two phases being arranged as concentric shells on an inert support. To prepare the shell catalyst, an aqueous slurry of the active materials is sprayed onto the support bodies with the aid of a coating drum or of a fluidized bed coater. A binder can be added to the slurry. Suitable binders specified are higher alcohols, DMF, cyclic ureas, etc., and polymeric binders such as vinyl acetate/vinyl laurate copolymers. The use of inorganic binders is not described.

WO 2005/037427 describes a catalyst bed composed of a physical mixture of catalytically active and catalytically inactive shaped bodies, the catalytically inactive shaped bodies having rounded edges on the outer friction surfaces. When the catalyst bed is used for the oxidation of methanol to formaldehyde, the catalytically active material used may, for example, be iron molybdates.

EP 0 184 790 describes a shaped catalyst for heterogeneously catalyzed reactions, which consists of an inert support material shaped to hollow cylinders, on which a catalytically active material is applied. The external diameter of the hollow cylinder is from 3 to 20 mm and the internal diameter is from 0.1 to 0.7 times the external diameter. The end surface of the hollow cylinder is curved such that the radius of curvature is from 0.4 to 5 times the external diameter. The catalysts are suitable especially for partial oxidations in the gas phase.

However, there is a demand for improved catalysts for oxidizing methanol to formaldehyde, which, as well as a very good abrasion resistance, also have a good activity and selectivity. It was therefore an object of the present invention to provide improved catalysts, especially for the oxidation of methanol to formaldehyde, which have a particularly high abrasion resistance and avoid the disadvantages of the prior art.

This object is achieved according to claim 1 by a shell catalyst or coated catalyst, especially for oxidation of methanol to formaldehyde, which, on an inert, preferably essentially nonporous, support body, has at least one coating which comprises, before the removal of the organic fractions of components b) and c):

a) oxides, or precursor compounds convertible to the corresponding oxides, of molybdenum and iron, where the molar ratio of Mo:Fe is between 1:1 and 5:1, and optionally further metallic components or metal oxide components or precursor compounds convertible to the corresponding oxides, b) at least one organic binder, preferably an aqueous dispersion of copolymers, especially selected from vinyl acetate/vinyl laurate, vinyl acetate/ethylene, vinyl acetate/acrylate, vinyl acetate/maleate, styrene/acrylate or mixtures thereof, c) and at least one further component selected from the group consisting of $SiO_2$ sol or precursors thereof, $Al_2O_3$ sol or precursors thereof, $ZrO_2$ sol or precursors thereof, $TiO_2$ sol or precursors thereof, waterglass, MgO, cement, monomeric, oligomeric or polymeric silanes, alkoxysilanes, aryloxysilanes, acryloyloxysilanes, aminosilanes, siloxanes or silanols.

It has thus been found that, surprisingly, a coated catalyst or shell catalyst in which the coating composition of the support body, as well as the (catalytically) active composition comprising oxides or precursor compounds of molybdenum and iron which are convertible to the corresponding oxides (component a)), comprises a combination of at least one organic binder which is removed (burnt out) in the course of heat treatment or calcination, and at least one further component selected from the group of $SiO_2$ sol and precursors thereof, $Al_2O_3$ sol and precursors thereof, $ZrO_2$ sol and precursors thereof, $TiO_2$ sol and precursors thereof, waterglass, MgO, cement, monomeric, oligomeric or polymeric silane, alkoxysilane, aryloxysilane, acryloyloxysilane, aminosilane, siloxane or silanols exhibits a particularly high abrasion resistance. At the same time, it has been found that, unexpectedly, not only are the heat-untreated inventive coated catalysts, i.e. those comprising the organic parts of the coating composition, particularly abrasion-resistant, but there is still a particularly high abrasion resistance after the heat treatment or calcination of the inventive catalysts, and a porosimetry particularly favorable for the activity of the catalyst for the oxidation of methanol to formaldehyde is provided. In this case, the (as yet heat-untreated and uncalcined) catalyst in which the organic fractions of components b) and c) are yet to be removed can also be considered as a catalyst precursor or precursor catalyst. In the finished catalyst, as used for oxidation of methanol to formaldehyde, the organic fractions of components b) and c) are then removed, especially by heat treatment or calcination.

Stated in simplified terms, the coating in the inventive coated catalysts, as well as the active composition (component a)), also comprises at least two components active as adhesion promoters. Of these, at least one component is an organic binder (component b)) which can be removed in the course of heat treatment and calcination of the catalyst. The second component (component c)) has at least one inorganic fraction or comprises a purely inorganic compound which, after the heat treatment or calcination of the coated catalyst, can advantageously form bridges between the oxidic constituents of the active composition, i.e. the molybdenum- and/or iron-containing oxides. The inorganic component or its inorganic fraction, without the invention being restricted to the correctness of the theoretical mechanism, apparently forms bonds between the primary particles of the iron oxides and/or molybdenum oxides, especially of the iron-molybdenum mixed oxide or of the other catalytically active components (a)). The organic compound b) and, where present, the organic fractions of the component c) (see above), in close association with the primary particles of the catalytically active component a), but without impairing the bridging thereof by the adhesion-promoting inorganic component or the inorganic fractions thereof, enable the formation of pores and hence, in the finished catalyst, the optimal access of the reactants to the active sites. In a particularly preferred embodiment, the component b) used is an organic binder from the group mentioned above. The use of this organic binder has the advantage that the coating operation can be accomplished in a fluidized bed apparatus with a particularly low level of spray losses. In addition, an advantageous pore structure forms at its removal.

According to the invention, the coated catalyst at first comprises an inert support body. It is possible here in principle to use all inert support bodies familiar to the person skilled in the art. The support bodies should, however, preferably be essentially nonporous and have a BET surface area (determined to DIN 66131) of less about 1 m²/g. The pore volume of the inert, essentially nonporous support body should preferably be less than 0.1 ml/g, determined to DIN 66133. The material density of the support bodies is preferably in the range from 2.0 to 4.5 g/cm³, especially preferably from 2.3 to 3.5 g/cm³. Examples of suitable support bodies are those composed of magnesium silicate (steatite), quartz ($SiO_2$), porcelain, magnesium oxide, tin oxide, silicon carbide, rutile, alumina ($Al_2O_3$), zirconium silicate, aluminum silicate, cerium silicate, or of mixtures of these support materials. Particular preference is given to steatite support bodies. It has been found that carbide-containing or sintered iron oxide support bodies provide poorer results.

In a preferred embodiment of the invention, the inert support bodies used are hollow cylinders. In a further preferred embodiment, the support body hollow cylinders used have one of the following sizes (external diameter×height×internal diameter):

6×5×3, 6×5×4, 6×4×4, 6×4×3, 5×5×3, 4×4×2, 4×4×1.5, 5×4×3, 5×5×2.5, 5×3×3, 4×3×1.5, 4×3×2, 3×3×1.5, 3×4×1.5, in each case in mm.

It has also been found that, surprisingly, particularly good results can be obtained with the inventive catalyst in the oxidation of methanol to formaldehyde when the support body hollow cylinders have at least one, preferably exactly one, central passage channel, and the end sides (exit sides of the passage channel) have (only) edges flattened on the outside, i.e. end surfaces which run at an acute angle (especially 10-90° C., more preferably 30-85°, even more preferably 40-80°) relative to the axis of the passage channel; see FIG. 1. It is also possible to use shaped bodies according to EP 1 127 618 A1 or WO 2005/037427 A1.

The above-described preferred support bodies in the shape of a cylinder with a passage channel and edges flattened on the outside at the ends offer the following advantages:

1. In the course of loading of the reactor, the shaped bodies do not as easily form locally ordered tight packings, but rather are arranged more irregularly, in which case more turbulences arise in the gas flow through the catalyst bed, which counter any slight onset of overheating, especially in the course of oxidation of methanol to formaldehyde. The reduction of the overheating also leads to an extension of the lifetime of the catalyst.
2. In the course of preparation of the catalyst in the preferred fluidized bed coater, there is less fracture at the edges than in the case of use of cylindrical bodies without flattened edges.
3. In the course of filling of the catalyst, the support with flattened edges fit together less than in the case of use of cylindrical bodies without flattened edges. This is especially true for the case that the value of reaction diameter to catalyst diameter is between about 2 and 5. The fitting together of the particles leads to filling gaps.

At least one layer (shell) of a coating composition which initially comprises, as an active component a), at least one molybdenum compound and at least one iron compound or at least one Fe- and Mo-containing compound, where the molar ratio of Mo:Fe is preferably between about 1:1 and 5:1, is applied to the inert support body. Preference is given to using oxides of molybdenum or iron and/or mixed oxides thereof (such as $Fe_2(MoO_4)_3$) or compounds which can be converted to the corresponding oxides or mixed oxides, for example acetates, oxalates, acetylacetonates, citrates, nitrates, chlorides, phosphates, sulfates, or ammonium compounds of iron or of molybdenum. In a particularly preferred embodiment of the invention, an iron-molybdenum mixed oxide ($Fe_2(MoO_4)_3$) is used as the iron-containing compound, and $MoO_3$ as the molybdenum-containing compound. In addition, in the above component a), it is also optionally possible for further metallic components or metal oxide components, or compounds which can be converted to the corresponding oxides or mixed oxides, to be present, which are familiar to the person skilled in the art with regard to the use of the catalyst for oxidation of methanol to formaldehyde. Nonrestrictive examples are the lanthanide metals and oxides thereof. Preference is given to titanium, antimony, tin, nickel, cerium, aluminum, calcium, magnesium, chromium, vanadium, niobium, silver and/or manganese, which may also partly replace Fe and Mo.

According to the invention, the coating of the inventive catalyst (before the removal of the organic fractions) comprises at least one organic binder (component b)). This binder improves the abrasion resistance of the coating and contributes to good adhesion of the coating on the inert support body. In addition, when an organic binder as defined herein is used, a particularly low spray loss and hence a particularly high application yield in the course of coating of the inert support bodies in the fluidized bed process (fluidized bed coater) are also achieved. In addition, it contributes to the formation of advantageous pores after the removal of the organic fractions of the coating composition. It has now been found that particularly advantageous results are obtained with aqueous dispersions of copolymers, especially vinyl acetate/vinyl laurate, vinyl acetate/ethylene, vinyl acetate/acrylate, vinyl acetate/maleate, or styrene/acrylate as organic binders. Such copolymers are familiar as such to those skilled in the art, can be prepared by standard methods and are commercially available. Suitable dispersions preferably have a solids content in the range from 20 to 80% by weight, preferably 40-60% by weight. Suitable binders include, for example, binder dispersions in which the binder is a copolymer of an alpha-olefin and of a vinyl $C_2$-$C_4$-carboxylate, whose vinyl $C_2$-$C_4$-carboxylate content is at least 62 mol %, as specified, for example, in WO 2005/011862.

In addition, the coating composition of the inventive coated catalysts comprises at least one further component (c)) selected from the group consisting of $SiO_2$ sol or precursors thereof, $Al_2O_3$ sol or precursors thereof, $ZrO_2$ sol or precursors thereof, $TiO_2$ sol or precursors thereof, waterglass, MgO, cement, monomeric, oligomeric or polymeric silane, alkoxysilane, aryloxysilane, acryloyloxysilane, aminosilane, siloxane or silanols. These compounds are familiar as such to those skilled in the art, can be prepared by standard methods and are commercially available.

Among the particularly preferred components, mention should be made here of the inorganic sols, especially $TiO_2$ sols, cerium oxide sols and $ZrO_2$ sols, since particularly good abrasion resistances and simultaneously high activities of the finished catalysts have been obtained here in the oxidation of methanol to formaldehyde.

According to the sol, the solids content is between 10 and 50% by weight; for example, preference is given to $SiO_2$ sols with solids content 20-40% by weight, $ZrO_2$ sols with solids content 10-20% by weight, $CeO_2$ sols with solid content 15-25% by weight and $TiO_2$ sols with solids content 10-20% by weight. $TiO_2$ sols are particularly preferred.

It has been found that, unexpectedly, the above components b) and c) cooperate in the generation of an optimal abrasion resistance and porosimetry of the catalyst. As a result of the adhesion promoter combination used in accordance with the invention (combination of the at least one component b) and at least one component c)), both adhesion and advantageous application of the coating composition or of the active material (component a)) on the shaped body, especially in the preferred fluidized bed process, and an open-pore structure and good adhesion of the active composition after the heat treatment or calcination of the catalyst are provided.

In a preferred embodiment of the invention, the integral pore volume (determined by Hg porosimetry, DIN 66133) is between about 100-800 $mm^3/g$, preferably between about 200 and 700 $mm^3/g$, more preferably between about 250 and 600 $mm^3/g$. The mean pore radius determined by this method is preferably between about 50 and 1000 nm, preferably between about 100 and 700 nm, more preferably between about 150 and 500 nm.

It has also been found that, surprisingly, the inventive heat-untreated catalyst (precursor catalyst), i.e. before the removal of the organic fractions of the coating composition, has a greatly improved transport and filling stability. One aspect of the present invention thus also relates to the use of an inventive catalyst, before the removal of the organic fractions of the coating composition (i.e. as a precursor catalyst), for the transport from the production site of the catalyst (or precursor catalyst) to the site of use of the catalyst, especially in the oxidation of methanol to formaldehyde. A further aspect relates to the use of such an inventive catalyst before the removal of the organic fractions of the coating composition (i.e. as a precursor catalyst) to fill a reactor, especially for oxidation of methanol to formaldehyde.

In a preferred embodiment of the invention, the component c) used is at least one sol with a particle size of 1 to 100 nm, preferably from 2 to 50 nm, more preferably <40 nm. These particle sizes were determined to ASTM B822-97. Alternatively, ISO 13320-1 can also be used.

More preferably, component c) has a smaller mean particle size than component(s) a).

It is particularly preferred in this case that component c) comprises a $ZrO_2$ sol, a $CeO_2$ sol, a $TiO_2$ sol or a mixture of two or all three of the above components. Moreover, it has been found that, surprisingly, particularly good abrasion resistances are obtained with a $TiO_2$ sol which has been stabilized with nitric acid or with citric acid. In addition, good abrasion resistances have been found with a $CeO_2$ sol stabilized with acetic acid or a mixture of the $TiO_2$ sol and the $CeO_2$ sol. It is particularly advantageous in this case when the $TiO_2$ sol is present in excess over the $CeO_2$ sol. In addition, good abrasion resistances have been found with a $ZrO_2$ sol which has been stabilized with acetate.

In addition to the sols provided in a solvent, it is also possible to use so-called aerosols, i.e. metal oxides which are provided as a solid with a very high specific surface area. Such finely divided solids can be prepared, for example, by flame hydrolysis, for example $SiO_2$ by hydrolysis of $SiCl_4$ in an $H_2/O_2$ flame. By comparable processes, it is also possible to prepare the other oxides mentioned above in finely divided form. However, the use of sols provided in a solvent is preferred, since the use of these sols leads to catalysts which exhibit a particularly high abrasion resistance. Moreover, in the case of use of sols in solvents, particularly low spray losses are achieved in the coating of the support bodies.

In a preferred embodiment of the invention, the solids content of component c) (i.e., for example, $ZrO_2$ or $TiO_2$), after the removal of the organic fractions of components b) and/or c), especially after the calcination or heat treatment of the catalyst (i.e. in the finished catalyst), is between about 0.01 and 30% by weight, preferably between 0.05 and 20% by weight, more preferably between 0.1 and 10% by weight, based on the catalytically active coating composition, i.e. the material of the shell. The corresponding use amounts of component c) can thus be determined easily by the person skilled in the art according to the component c) and component a) used.

Moreover, it is preferred in accordance with the invention that the solids content of component b) is between 5 and 30% by weight, preferably between about 8 and 25% by weight, based on the catalytically active coating composition, i.e. the material of the shell. These data are of course based on the state before the removal of the organic fractions of the coating composition.

In a further preferred embodiment of the invention, the active composition content (component (a)/(component (a)+ inert support)) is between about 3 and 60% by weight, preferably between about 3 and 50% by weight, more preferably between about 5 and 40% by weight, based on the mass of inert support and catalytically active material. The geometries of the inert support bodies typically used give rise to a thickness, which is preferred in accordance with the invention, of the coating on the inert support body between about 30 and 1000 μm, preferably between about 100 and 700 μm.

In a preferred embodiment of the invention, in the inventive catalyst, after the removal of the organic fractions of the coating composition, the integral pore volume (to DIN 66133) based on the active composition is more than about 0.15 $ml/g_{active\ composition}$, preferably more than 0.2 $ml/g_{active\ composition}$.

A further aspect of the present invention relates to a process for preparing an inventive coated catalyst, especially for oxidizing methanol to formaldehyde, comprising the following steps:
a) providing an inert, preferably essentially nonporous, support body,
b) preparing an aqueous suspension comprising components a), b), c) as defined above,
c) applying the aqueous suspension of step b) to the inert support body, preferably in a fluidized bed process.

In a first step, an inert, preferably essentially nonporous, support body as described above is provided.

In addition, an aqueous suspension comprising components a), b), c), as described above, is provided. In this context, it has been found to be particularly advantageous in accordance with the invention that all components a), b) and c) are present in particle form, either suspended or dispersed, and not in dissolved form. The solids content in the suspension/dispersion is preferably between 5 and 40% by weight, more preferably between 10 and 30% by weight.

In the process according to the invention, it is preferred that the aqueous suspension provided is applied to the inert support body by means of a fluidized bed process. Preference is given to the use of a fluidized bed coater, as described, for example, in DE-A-12 80 756, DE-A-197 09 589, DE 40 06 935 A1, DE 103 44 845 A1 or WO 2005/030388. It has been found in accordance with the invention that the aqueous suspension comprising the coating composition can be applied to the nonporous support body by means of a fluidized bed process, as detailed above, particularly uniformly and with good adhesion and with unexpectedly low spray losses.

In addition, it has been found to be advantageous that the pH of the suspension is matched to the stability range of component b) and component c). It has been found that, for this purpose, a pH of the suspension to be applied to the support bodies of between about 1 and 5 is generally advantageous. It has also been found that a pH of about 3-5 is advantageous in the case of use of an acetate-stabilized $ZrO_2$ sol, or a pH between 1 and 5, preferably between 1 and 3, in the case of use of a $TiO_2$ sol stabilized with nitric acid. In the case of the $CeO_2$ sol stabilized with acetic acid, a pH of 2-4 is particularly advantageous.

In addition, it has been found that particularly favorable results are obtained when component a) is not heated to more than 200° C., and is especially not heat treated or calcined, before being applied to the inert support body.

However, it is possible in one embodiment to calcine the active material (component a) before it is applied to the inert support body, in order, for example, to adjust its activity. However, preference is given to introducing the catalyst into the reactor in a form in which the shell of the catalyst comprises the uncalcined or low-calcination material and the organic binder. The active material can then be calcined simultaneously with the burning-off of the organic binder.

In a further preferred embodiment of the invention, the aqueous suspension is applied to the inert support bodies in a fluidized bed process at a temperature of less than 100° C., especially at less than 80° C., more preferably less than 70° C.

The particles of components a), b) and c) in the aqueous suspension preferably have a $D_{90}$ value of the particle size of less than 50 μm, preferably less than 30 μm. Adhering to this particle size contributes to a particularly uniform and abrasion-resistant coating on the inert support bodies and leads to low spray losses during the coating operation. If materials which have the above particle size are not used in any case for components a), b) and c), this particle size can be established by conventional grinding or comminition before, during or after the preparation of the aqueous suspension.

In a further preferred embodiment, after the application of the coating composition to the inert support body, the coated support body is treated thermally. In general, any temperature and duration for calcination or for heat treatment familiar to the person skilled in the art can be used. In many cases, a temperature between 200 and 600° C., especially 200 and 550° C., will be advantageous. The duration of the calcination or of the heat treatment will preferably be between 0.5 and 20 h, especially between 1 and 15 h. In a preferred embodiment, the coated support body will be introduced into a suitable heated cabinet, for example a tray oven with metal sheets, which contains the coated support bodies as a particle bed with a preferred bed height of 1-5 cm, more preferably of 1-3 cm. The heated cabinet is then preferably heated with a constant rate within a period of from 1 h to 20 h, preferably from 5 h to 15 h, from room temperature to a temperature T1 of preferably between 130 and 350° C., especially preferably from 200 to 300° C. The heating rate for the above-described process step is preferably selected within the range from 0.1 to 5° C./min, more preferably from 0.2 to 1° C./min. The temperature T1 is then preferably kept constant for the duration of from 1 h to 5 h. Subsequently, the temperature is heated at a preferably constant rate, within a period of from 1 h to 10 h, preferably from 1 h to 5 h, proceeding from the temperature T1 to an end temperature T2 between 300 and 600° C., preferably from 350 to 550° C., more preferably from 400° C. to 550° C. The heating rate for the above-described process step is preferably selected within the range from 0.1 to 10° C./min, more preferably from 2 to 5° C./min. The temperature T2 is maintained for a duration of 1-10 h, preferably of 2-5 h, and the heated cabinet is then cooled. Preference is given to selecting a cooling rate of 1-10° C./min, more preferably of 2-8° C./min. During the thermal treatment, it may be advantageous to flow air or a mixture of air, nitrogen and optionally steam whose composition varies with time through the gas space of the heated cabinet.

The organic binders preferred as component b) according to the above description have the advantage that they, even at the above relatively low coating temperatures in the fluidized bed coater, contribute very efficiently to the adhesion and abrasion resistance of the coating composition, and can simultaneously be removed at the temperatures preferred for the heating or calcination of the coated catalyst after the application of the coating to the inert support body without impairing the adhesion and abrasion resistance of the coating, in order to contribute to an advantageous pore structure.

In a preferred embodiment of the invention, the above-described heating after the application of the coating to the inert support body is effected in an atmosphere of air, inert gas and/or steam. When the heating is effected in the presence of steam, preference is given to a steam content of more than about 10% by volume, preferably between about 20 and 60% by volume, of the atmosphere used.

If, as stated above, in a preferred aspect of the present invention, the inventive coated catalyst before the removal of the organic fractions of the coating composition is itself used to fill the reactor, it has also been found in the context of the present invention that the removal of the organic fractions of the coating composition (by means of heating or heat treatment or calcination of the catalyst) advantageously also directly in the reactor itself, especially in an $O_2$- and $N_2$-containing gas stream to which steam may optionally be added. The conditions for the calcination or the removal of the organic binder are preferably selected according to the conditions already described for the treatment of the catalyst. In a further preferred embodiment, the calcination can also take place under the operating conditions envisaged for the finished catalyst, such as the conditions of the envisaged methanol oxidation to formaldehyde.

A further aspect of the invention relates to a catalyst obtainable by the above process. Such catalysts are notable for an increased abrasion resistance compared to prior art catalysts. Moreover, by virtue of an advantageous porosimetry after the removal of the organic fractions of the coating composition, a high activity and formaldehyde selectivity, especially in the oxidation of methanol, is ensured for the catalysts.

A further aspect of the present invention thus relates to the use of the above-described coated catalyst for oxidizing methanol to formaldehyde, especially in a fixed bed process. A suitable process is known, for example, from DE 103 61 517, EP 0 001 570 and U.S. Pat. No. 3,852,361. It is also possible to use other processes familiar to those skilled in the art for preparing formaldehyde. However, other applications of the catalyst, especially in partial (gas phase) oxidations of hydrocarbons, are not ruled out in principle.

The gas phase oxidation is itself carried out in the reactors known for this reaction under customary conditions. Preference is given to tubular reactors, in which case the tubes are cooled for heat removal, for example, with a salt bath or a thermally stable oil. The tubes preferably have a diameter in the range from 15 to 30 mm, more preferably of 20-25 mm, and a length in the range of preferably from 80 to 140 cm. The inventive catalyst is filled into the tubes.

A further aspect of the invention relates to the use of a combination of the above-described components b) and c) to increase the abrasion resistance of a coated catalyst, especially of a catalyst for the oxidation of methanol to formaldehyde.

FIG. 1 shows a cross section through a support body used with preference in accordance with the invention, with edges flattened on the outside at the ends. The acute angle α between the axis of the central passage orifice and the end faces is in each case about 60 degrees.

DEFINITIONS OF TERMS a) Active composition content=mass of active composition (component a))/(mass of active composition (component a))+mass of support body)
b) Solids content of component b=mass of solid in the org. binder (component b))/(mass of solid in the org. binder (component b))+mass of active composition (component a)))
c) Solids content of component c=mass of solid in component c)/(mass of solid in component c)+mass of active composition (component a)))

According to the invention, the following determination methods were used:

1. Test for Determining the Adhesion of the Active Composition (Abrasion Test):

The adhesion of the active composition was tested in an instrument from ERWEKA, model: TAR 10. To this end, an amount of 50 g of coated catalyst was rotated a total of 10 times at a rotational speed of 75 revolutions/min (=10 rotations of the drum). Thereafter, the abrasion was determined as the ratio of the loose coating no longer bonded to the support body relative to the total amount of coating applied.

2. BET Surface Area:

The determination was effected by the BET method to DIN 66131; a publication of the BET method is also found in J. Am. Chem. Soc. 60, 309 (1938).

3. Pore Radius Distribution:

The pore radius distribution was determined mercury porosimetry to DIN 66133; maximum pressure: 2000 bar, Porosimeter 4000 (from Porotec, Germany), according to the manufacturer's instructions.

4. Determination of the Particle Sizes:

The particle sizes were determined by the laser diffraction method with a Fritsch Particle Sizer Analysette 22 Economy (from Fritsch, Germany) according to the manufacturer's instructions, also with regard to the sample pretreatment: the sample is homogenized in deionized water without addition of assistants and treated with ultrasound for 5 minutes. The D values reported are based on the sample volume.

The invention is illustrated in detail with reference to the nonrestrictive examples which follow:

EXAMPLE 1 (INVENTIVE)

To prepare the inventive catalyst with an active composition content (component a)) of 20% by weight, a solids content of an organic binder (component b)) of 20% by weight and a solids content of the inorganic adhesion-promoting component c)) of 1% by weight, 700 g of steatite bodies (density 2.7 g/cm$^3$) in the form of hollow cylinders of dimensions 5×5×2.5 mm were coated in a fluidized bed coater with a suspension which was prepared as follows:

A glass vessel was initially charged with 1100 ml of demineralized water. 184 g of the active composition powder (mixture of $Fe_2(MoO_4)_3$ and $MoO_3$, prepared according to example 1 of EP 1 674 156 A1 (molar Mo:Fe ratio=2.5)) are suspended with stirring. For better homogenization, the suspension is treated with an Ultra-Turrax® at level 6 for 3 min. With stirring, 9.22 g of the $ZrO_2$ sol (solids content 20%, acetate-stabilized, from Nyacol, trade name: NYACOL® Zirconia (Acetate)) are added thereto. The pH of the suspension is adjusted to 4 with a 25% ammonia solution. To the suspension are added 92 g of the organic binder (50% dispersion of water and vinyl acetate/ethylene copolymer, Vinnapas® EP 65 W, from Wacker), and the suspension is homogenized with stirring for one hour.

The coating composition thus obtained is applied to the steatite bodies in a fluidized bed in the form of thin layers at a temperature between 60-80° C. The layer thickness of the catalytically active material on the outer wall of the hollow cylinder was 300 μm.

At a temperature of 400° C. or 500° C., a portion of the coated catalyst was treated thermally under air for a period of 2 hours, in the course of which the organic fractions of the coating composition (the organic binder) were removed. The abrasion of the catalyst calcined at 400° C. was 1.3% by weight; the abrasion of the catalyst calcined at 500° C. was 3.1% by weight. The abrasion of the uncalcined catalyst was <<1%.

The integral pore volume measured by means of Hg porosimetry is 0.42 ml/g for the catalyst calcined at 400° C., and 0.37 ml/g for the catalyst calcined at 500° C.

EXAMPLE 2 (INVENTIVE)

To prepare the inventive catalyst with an active composition content (component a)) of 20% by weight, a solids content of an organic binder (component b)) of 20% by weight and a solids content of the inorganic adhesion-promoting component c)) of 4.7% by weight, 700 g of steatite bodies (density 2.7 g/cm$^3$) in the form of hollow cylinders of dimensions 5×5×2.5 mm were coated in a so-called fluidized bed coater with a suspension which was prepared as follows:

A glass vessel was initially charged with 1100 ml of demineralized water. 184 g of the active composition powder (mixture of $Fe_2(MoO_4)_3$ and $MoO_3$, prepared according to example 1 of EP 1 674 156 A1 (molar (Mo:Fe ratio=2.5)) are suspended with stirring. For better homogenization, the suspension is treated with an Ultra-Turrax® at level 6 for 3 min. With stirring, 76 g of the $TiO_2$ sol (solids content 12%, stabilized with nitric acid, from Sachtleben, trade name: Hombikat™ XXS 100) are added thereto. The pH of the suspension was 2.2. To the suspension are added 92 g of the organic binder (50% dispersion of water and vinyl acetate/ethylene copolymer, Vinnapas® EP 65 W, from Wacker), and the suspension is homogenized with stirring for one hour.

The coating composition thus obtained is applied to the steatite bodies in a fluidized bed in the form of thin layers at a temperature between 60-80° C. The layer thickness of the catalytically active material was 305 μm.

At a temperature of 400° C. or 500° C., a portion of the coated catalyst was treated thermally under air for a period of 2 hours, in the course of which the organic fractions of the coating composition (the organic binder) were removed. The abrasion of the catalyst calcined at 400° C. was 2.7% by weight; the abrasion of the catalyst calcined at 500° C. was 5.3% by weight. The abrasion of the uncalcined catalyst was <<1%.

The integral pore volume measured by means of Hg porosimetry is 0.44 ml/g for the catalyst calcined at 400° C., and 0.38 ml/g for the catalyst calcined at 500° C.

EXAMPLE 3 (INVENTIVE)

To prepare the inventive catalyst with an active composition content (component a)) of 26% by weight, a solids content of an organic binder (component b)) of 20% by weight and a solids content of the inorganic adhesion-promoting component c)) of 4.7% by weight, 700 g of steatite bodies (density 2.7 g/cm$^3$) in the form of hollow cylinders of dimensions 5×5×2.5 mm were coated in a fluidized bed coater with a suspension which was prepared as follows:

A glass vessel was initially charged with 1100 ml of demineralized water. 245 g of the active composition powder (mixture of Fe$_2$(MoO$_4$)$_3$ and MoO$_3$, prepared according to example 1 of EP 1 674 156 A1 (molar (Mo:Fe ratio=2.5)) are suspended with stirring. For better homogenization, the suspension is treated with an Ultra-Turrax® at level 6 for 3 min. With stirring, 46 g of the cerium oxide sol (solids content 20%, 3% acetic acid) are added thereto. The pH of the suspension is adjusted to 4 with a 25% ammonia solution. To the suspension are added 122 g of the organic binder (50% dispersion of water and vinyl acetate/ethylene copolymer, Vinnapas® EP 65 W, from Wacker), and the suspension is homogenized with stirring for one hour.

The coating composition thus obtained is applied to the steatite bodies in a fluidized bed in the form of thin layers at a temperature between 60-80° C. The layer thickness of the catalytically active material was 424 μm.

At a temperature of 400° C. or 500° C., a portion of the coated catalyst was treated thermally under air for a period of 2 hours, in the course of which the organic fractions of the coating composition (the organic binder) were removed. The abrasion of the catalyst calcined at 400° C. was 0.7% by weight; the abrasion of the catalyst calcined at 500° C. was 1.3% by weight. The abrasion of the uncalcined catalyst was <<1%.

The integral pore volume measured by means of Hg porosimetry is 0.41 ml/g for the catalyst calcined at 400° C., and 0.37 ml/g for the catalyst calcined at 500° C.

EXAMPLE 4 (INVENTIVE)

To prepare the inventive catalyst with an active composition content (component a)) of 20% by weight, a solids content of an organic binder (component b)) of 20% by weight and a solids content of the inorganic adhesion-promoting component c)) of 4.7% by weight, 700 g of steatite bodies (density 2.7 g/cm$^3$) in the form of hollow cylinders of dimensions 5×5×2.5 mm were coated in a fluidized bed coater with a suspension which was prepared as follows:

A glass vessel was initially charged with 1100 ml of demineralized water. 184 g of the active composition powder (mixture of Fe$_2$(MoO$_4$)$_3$ and MoO$_3$, prepared according to example 1 of EP 1 674 156 A1 (molar (Mo:Fe ratio=2.5)) are suspended with stirring. For better homogenization, the suspension is treated with an Ultra-Turrax® at level 6 for 3 min. With stirring, 46 g of the SiO$_2$ sol (GRACE Davidson, solids content 30%, trade name: Ludox® AS-30) are added thereto. The pH of the suspension is adjusted to 4 with a 25% ammonia solution. To the suspension are added 92 g of the organic binder (50% dispersion of water and vinyl acetate/ethylene copolymer, Vinnapas® EP 65 W, from Wacker), and the suspension is homogenized with stirring for one hour.

The coating composition thus obtained is applied to the steatite bodies in a fluidized bed in the form of thin layers at a temperature between 60-80° C. The layer thickness of the catalytically active material was 300 μm.

At a temperature of 400° C. or 500° C., a portion of the coated catalyst was treated thermally under air for a period of 2 hours, in the course of which the organic fractions of the coating composition (the organic binder) were removed. The abrasion of the catalyst calcined at 400° C. was 2.7% by weight; the abrasion of the catalyst calcined at 500° C. was 4.2% by weight. The abrasion of the uncalcined catalyst was <<1%.

The integral pore volume measured by means of Hg porosimetry is 0.39 ml/g for the catalyst calcined at 400° C., and 0.35 ml/g for the catalyst calcined at 500° C.

EXAMPLE 5 (COMPARATIVE)

To prepare the comparative catalyst with an active composition content (component a)) of 21% by weight and a solids content of the organic binder (component b)) of 20% by weight, 700 g of steatite bodies (density 2.7 g/cm$^3$) in the form of hollow cylinders of dimensions 5×5×2.5 mm were coated in a fluidized bed coater with a suspension which was prepared as follows:

A glass vessel was initially charged with 1100 ml of demineralized water. 184 g of the active composition powder (mixture of Fe$_2$(MoO$_4$)$_3$ and MoO$_3$, prepared according to example 1 of EP 1 674 156 A1 (molar (Mo:Fe ratio=2.5)) are suspended with stirring. For better homogenization, the suspension is treated with an Ultra-Turrax® at level 6 for 3 min. The pH of the suspension is adjusted to 4 with a 25% ammonia solution. To the suspension are added 92 g of the organic binder (50% dispersion of water and vinyl acetate/ethylene copolymer, Vinnapas® EP 65 W, from Wacker), and the suspension is homogenized with stirring for one hour.

The coating composition thus obtained is applied to the steatite bodies in a fluidized bed in the form of thin layers at a temperature between 60-80° C. The layer thickness of the catalytically active material was 312 μm.

At a temperature of 400° C. or 500° C., a portion of the coated catalyst was treated thermally for a period of 2 hours, in the course of which the organic binder was removed. The abrasion of the catalyst calcined at 400° C. was 37.9% by weight; the abrasion of the catalyst calcined at 500° C. was 38.3% by weight. The abrasion of the uncalcined catalyst was somewhat below 1% and significantly higher than in the case of the above inventive catalyst.

The integral pore volume measured by means of Hg porosimetry is 0.46 ml/g for the catalyst calcined at 400° C., and 0.42 ml/g for the catalyst calcined at 500° C.

The invention claimed is:

1. A coated catalyst, especially for oxidation of methanol to formaldehyde, which, comprises an inert, preferably essentially nonporous, support body, with at least one coating which comprises, before the removal of the organic fractions of components b) and c):
   a) oxides, or precursor compounds convertible to the corresponding oxides, of molybdenum and iron, where the molar ratio of Mo:Fe is between 1:1 and 5:1,
   b) at least one organic binder,
   c) and at least one further component selected from the group consisting of SiO$_2$ sol or precursors thereof, Al$_2$O$_3$ sol or precursors thereof, ZrO$_2$ sol or precursors thereof, TiO$_2$ sol or precursors thereof, waterglass, CeO$_2$ sol, MgO, cement, monomeric, oligomeric or polymeric silanes, alkoxysilanes, aryloxysilanes, acryloyloxysilanes, aminosilanes, siloxanes and silanols.

2. The coated catalyst as claimed in claim 1, wherein the organic binder comprises an aqueous dispersion of copolymers selected from the group consisting of vinyl acetate/vinyl laurate, vinyl acetate/ethylene, vinyl acetate/acrylate, vinyl acetate/maleate, styrene/acrylate and mixtures thereof.

3. The coated catalyst as claimed claim 1, characterized in that molybdenum and iron are present in a form selected from the group consisting of oxides, mixed oxides and a mixture of mixed oxide and pure oxides.

4. The coated catalyst as claimed in claim 1, characterized in that component c) comprises at least one sol with a particle size from 1 to 100 nm.

5. The coated catalyst as claimed in claim 1, characterized in that component c) comprises a component selected from the group consisting of $TiO_2$ sol, $ZrO_2$ sol, or $CeO_2$ sol and a mixture of two or all three components.

6. The coated catalyst as claimed in claim 1, characterized in that the $ZrO_2$ sol is acetate-stabilized.

7. The coated catalyst as claimed in claim 1, characterized in that the $TiO_2$ sol is stabilized either with nitric acid or citric acid.

8. The coated catalyst as claimed in claim 1, characterized in that the $CeO_2$ sol is stabilized with acetic acid.

9. The coated catalyst as claimed in claim 1, characterized in that the solids content of component c) after removal of the organic fractions of components b) and c) and based on the catalytically active coating composition is between 0.01 and 30% by weight.

10. The coated catalyst as claimed in claim 1, characterized that the solids content of component b) based on the catalytically active coating composition and based on the state before removal of the organic fractions of the coating composition is between 5 and 30% by weight.

11. The coated catalyst as claimed in claim 1, characterized in that the inert support bodies used are hollow cylinders.

12. The coated catalyst as claimed in claim 11, characterized in that the hollow cylinders used have one of the following sizes (external diameter×height×internal diameter): 6×5×3, 6×5 33 4, 6×4×4, 6×4×3, 5×5×3, 4×4×2, 4×4×1.5, 5×4×3, 5×5×2.5, 5×3×3, 4×3×1.5, 4×3×2, 3×3×1.5, 3×4×1.5, in each case in mm.

13. The coated catalyst as claimed in claim 1, characterized in that the inert support body comprises a cylinder with a passage channel and edges flattened on the outside at the ends.

14. The coated catalyst as claimed in claim 1, characterized in that the active composition content is between about 3 and 60% by weight.

15. The coated catalyst as claimed in claim 1, characterized in that the thickness of the coating on the inert support is between about 30 and 1000 μm.

16. The coated catalyst as claimed in claim 1, characterized in that the inert support body has a porosity of less than 0.1 ml/g and a BET surface area of less than 1 $m^2/g$.

17. The coated catalyst as claimed in claim 1, characterized in that component a) further comprises further metallic components or metal oxide components selected from the group consisting of the lanthanides and their oxides.

18. The coated catalyst as claimed in claim 1, characterized in that component a) further comprises further metallic components or metal oxide components selected from the group consisting of titanium, antimony, tin, nickel, chromium, aluminum, calcium, magnesium, vanadium, niobium, silver and manganese.

19. The coated catalyst as claimed in claim 1, characterized in that the integral pore volume of the coating, after removal of the organic fractions of components b) and c), is greater than 0.2 ml/g.

20. A process for preparing the coated catalyst as claimed in claim 1, especially for oxidizing methanol to formaldehyde, comprising the following steps:
   a) providing an inert, preferably essentially nonporous, support body,
   b) preparing an aqueous suspension comprising components a), b), c) as defined in claim 1, and
   c) applying the aqueous suspension of step b) to the inert support body in a fluidized bed process.

21. The process as claimed in claim 20, characterized in that the application of the coating in a fluidized bed process is carried out at less than 100° C.

22. The process as claimed in claim 20, characterized in that components a) and b) from claim 1, are present in the aqueous suspension in the form of a suspension or dispersion and not in dissolved form.

23. The process as claimed in claim 20, characterized in that the pH of the aqueous suspension according to step b) of claim 20, when an acetate-stabilized $ZrO_2$ sol is used, is between about 3 and 5.

24. The process as claimed in claim 20, characterized in that the pH of the aqueous suspension according to step b) of claim 20, when a nitric acid-stabilized $TiO_2$ sol is used, is between about 1 and 3.

25. The process as claimed in claim 20, characterized in that the pH of the aqueous suspension according to step b) of claim 20, when an acetic acid-stabilized $CeO_2$ sol is used, is between about 2 and 4.

26. The process as claimed in claim 20, characterized in that component a) is not heated to more than 200° C., before being applied to the inert support body.

27. The process as claimed in claim 20, characterized in that the aqueous suspension has a particle size ($d_{90}$) of less than 50 μm.

28. The process as claimed in claim 20, characterized in that the particle sizes of components a), b) and c) are established by a grinding operation before, during or after preparation of the aqueous suspension.

29. The process as claimed in claim 20, characterized in that the coated catalyst is heated to a temperature between about 150 and 600° C., after being applied to the inert support body.

30. The process as claimed in claim 29, characterized in that the heating is effected in an atmosphere of air, inert gas and/or steam.

31. The process as claimed in claim 29, characterized in that the heating is effected as a calcination at a temperature between about 350 and 450° C.

32. The process as claimed in claim 29, characterized in that the heating rate in the course of heating or calcination is between 0.1 and 10° C./min.

33. The process as claimed in claim 29, characterized in that the steam content in the course of heating or calcination is more than 10% by volume, of the atmosphere used.

34. The process as claimed in claim 29, characterized in that the heating or calcination takes place directly within the reactor in an $O_2/N_2$ gas stream or under the operating conditions envisaged for the coated catalyst.

35. A process for oxidizing methanol to formaldehyde comprising the following steps:
   a) providing a catalyst according to claim 1 in a fixed bed,
   b) contacting the catalyst in the fixed bed with methanol in a gas stream in order to obtain formaldehyde by oxidation.

* * * * *